(12) United States Patent
Wiley (10) Patent No.: US 10,195,068 B2
(45) Date of Patent: Feb. 5, 2019

(54) METHOD AND APPARATUSES FOR POSITIONING A USER'S FOOT

(71) Applicant: David E. Wiley, Lansing, IA (US)

(72) Inventor: David E. Wiley, Lansing, IA (US)

(73) Assignee: David E. Wiley, Lansing, IA (US)

( * ) Notice: Subject to any disclaimer, the term of this patent is extended or adjusted under 35 U.S.C. 154(b) by 399 days.

(21) Appl. No.: 14/454,990

(22) Filed: Aug. 8, 2014

(65) Prior Publication Data

US 2015/0045709 A1 Feb. 12, 2015

Related U.S. Application Data

(60) Provisional application No. 61/958,873, filed on Aug. 8, 2013.

(51) Int. Cl.
*A61F 5/00* (2006.01)
*A61F 5/01* (2006.01)

(52) U.S. Cl.
CPC .................... *A61F 5/0111* (2013.01)

(58) Field of Classification Search
CPC ........ A61F 5/01; A61F 5/0102; A61F 5/0104; A61F 5/0111; A61F 5/0113; A61F 5/0116; A61F 5/0127; A61F 5/019; A61F 5/0585; A61F 5/14
See application file for complete search history.

(56) References Cited

U.S. PATENT DOCUMENTS

| | | | | |
|---|---|---|---|---|
| 1,575,042 A | * | 3/1926 | Denniston | ............. A61F 5/0585 602/27 |
| 2,755,488 A | | 7/1956 | Fuhrer | |
| 5,799,659 A | * | 9/1998 | Stano | .................... A61F 5/0111 128/882 |
| 6,349,487 B1 | | 2/2002 | Hice | |
| 7,794,417 B1 | * | 9/2010 | Zimmerman | ........... A61F 5/019 602/23 |
| 8,667,715 B2 | | 3/2014 | Santopietro et al. | |
| 2006/0000120 A1 | * | 1/2006 | Chenut | .................. A43B 7/142 36/144 |

(Continued)

FOREIGN PATENT DOCUMENTS

EP 0615704 B1 9/1994
WO 1994014391 A1 7/1994

OTHER PUBLICATIONS

Botte, R. "An interpretation of the pronation syndrome and foot types of patients with low back pain." Journal of the American Podiatry Association, 1981, vol. 71, 243-252. 1 page.

(Continued)

*Primary Examiner* — Kim M Lewis (57) ABSTRACT

Apparatuses and methods in accordance with embodiments of the invention include a rigid or semi-rigid platform having a first-toe side, a fifth-toe side laterally opposite the first-toe side, and a first support structure arranged in a midfoot region of the rigid or semi-rigid platform and laterally extending from the fifth-toe side to a portion of the midfoot region of the rigid or semi-rigid platform. The apparatuses and methods also include a lateral abutment arranged in the forefoot region of the rigid or semi-rigid platform and extending vertically from the rigid or semi-rigid platform near the first-toe side, the lateral abutment configured to laterally support the user's foot at the first toe.

12 Claims, 8 Drawing Sheets

(56) References Cited

U.S. PATENT DOCUMENTS

| | | | |
|---|---|---|---|
| 2006/0053664 A1* | 3/2006 | Tager | A61F 5/14 36/144 |
| 2006/0059726 A1* | 3/2006 | Song | A43B 7/142 36/142 |
| 2010/0242310 A1 | 9/2010 | Gourineni | |
| 2012/0210605 A1 | 8/2012 | Riley | |

OTHER PUBLICATIONS

D'Ambrosia, R. et al. "Prevention and Treatment of Running injuries." 1982, Orthotics. In R. D'Ambrosia & D Drez (Eds.),Thorofare, NJ: Slack. p. 157 4th paragraph. 1 page.

D'Amico, J. et al. "The influence of foot orthoses on quadriceps angle." 1986, Journal of the American Podiatry Association, vol. 76, 337-339. 3 pages.

Donatelli, R. "Abnormal biomechanics of the foot and ankle." 1987, The Journal of Orthopaedic and Sports Physical Therapy, vol. 9, 11-16. 1 page.

Donatelli, R. et al. "Biomechanical foot orthotics: A retrospective study." 1988, The Journal of Orthopaedic and Sports Physical Therapy, vol. 10, 205-212. 1 page.

Gill, E. "Orthotics." Feb. 1985, Runners's World. 55-57, p. 81 second column 3rd paragraph. 1 page.

Halbach, J. "Pronated foot disorders." 1981, Athletic Training, vol. 16, 53-55. 3 pages.

Hicks J. H. "The plantar aponeurosis and the arch." 1954, The mechanics of the foot. J Anat. 88(1): 25-30. Windlass mechanism and pronator twist p. 26. 6 pages.

Hughes, L. "Biomechanical analysis of the foot and ankle for predisposition to developing stress fractures." 1985, The Journal of Orthopaedic and Sports Physical Therapy, vol. 7, 96-101. 1 page.

Hunter, S. "Rehabilitation of foot injuries." 1990, In Prentice (Ed.), Rehabilitation Techniques in Sports Medicine, pp. 342-357. St. Louis: Times-Mirror/Mosby. 4 pages.

Hunter, S. et al. "Foot Orthotics in Therapy and Sports." Champaign, IL: Human Kinetics; 1995. Normal gait phases and function, p. 11-15. STJN theory: allows the foot to function in a more biomechanically correct manner, p. 4. 4 pages.

James, S. L. et al. "Injuries to Runners." 1978, The American Journal of Sports Medicine, vol. 6, 40-50. 5 pages.

Kendall, F. et al. "Muscle function in relation to posture." 1983, In Williams and Wilkins (Ed.), Muscles Testing and Function, pp. 270-277. Baltimore. 6 pages.

Mann, R. "Biomechanical approach to the treatment of foot problems." 1982, Foot and Ankle, vol. 2, 209-212. 8 pages.

McPoil and Cornwall (1994 Ankle Foot Interpg 141-145); taken from JOSPT (1995) Evaluation and Management of Foot and Ankle Disorders: Present problems and Future Directions Thomas G. McPoil, PhD, PT, ATC ' Gary C. Hunt, MA, PT, OCS. 1 page.

McPoil, T. et al. "Relationship Between Three Static Angles of the Rearfoot and the Pattern of Rearfoot Motion During Walking." 1996, Journal of Orthopaedic & Sports Physical Therapy. p. 370-375. 1 page.

Ramig, D. et al. "The foot and sports medicine: Biomechanical foot faults as related to chondromalacia patellae." 1980, The Journal of Orthopaedic and Sports Physical Therapy, vol. 2, 48-50. 1 page.

Rodger, M. et al. "Effectiveness of foot orthotic devices used to modify pronation in runners." 1982, The Journal of Orthopaedic and Sports Physical Therapy, vol. 4, 86-90. 1 page.

Root M. et al. "The Peroneus Longus Muscle." 1977, Clinical biomechanics: vol. II. Normal and abnormal function of the foot Los Angeles: Clinical Biomechanics. 2 pages.

Root, M. et al. "Measurement of Forefoot Varus and Forefoot Valgus." 1971, Clinical Biomechanics: vol. 1. Biomechanical Examination of the foot. Los Angeles: Clinical Biomechanics. 5 pages.

Saxena, A. et al. "The Effect of Foot Orthoses on Patellofemoral Pain Syndrome." 2003, Journal of American Podiatric Medical Association. 93(4): 264-271. 17. 1 page.

Speck, J. "Forefoot varus and over-pronation." Oct. 23, 2012, Somastruck, Somastruck.com. 2 pages.

Subotnick, S. "Bony Abnormalities of the Foot." 1975, Podiatric sports medicine. Mt. Kisco, NY: Futura. 6 pages.

Viitasalo, J. et al. "Some biomechanical aspects of the foot and ankle in athletes with and without shin splints." 1983, The American Journal of Sports Medicine, vol. 11, 125-130. 1 page.

\* cited by examiner

METHOD AND APPARATUSES FOR POSITIONING A USER'S FOOT

CROSS-REFERENCE TO RELATED APPLICATION

This application claims priority to Provisional Application No. 61/958,873, filed Aug. 8, 2014, which is herein incorporated by reference in its entirety.

TECHNICAL FIELD

The present invention relates to devices and methods for positioning a user's foot. More specifically, the invention relates to devices and methods that may be useful for treatment of certain types of foot and lower limb pain.

BACKGROUND

An over-pronation of a foot and ankle may lead to a fallen arch and splayed foot, described as pes planus, or partial dislocation of a talus (a bony structure of an ankle). This may result in a dysfunctional foot, which may cease to use a normal biomechanics. A dysfunctional gait cycle involving a pronated push-off may lead to an additional dysfunction/compensation such as a progressive pain and injury brought on by a potential bunion formation, progressive knock-knees, inwardly rotated hips, as well as a back dysfunction.

Previous attempts to address these problems have supported the foot and/or ankle by changing a weight bearing foot position during gait. This, however, further enhances the dysfunctional gait cycle rather than addressing the dysfunctional biomechanics of the foot.

SUMMARY

In Example 1, an apparatus for positioning a user's foot. The apparatus comprises a rigid or semi-rigid platform having a first-toe side, a fifth-toe side laterally opposite the first-toe region, a forefoot region, a midfoot region, and a rearfoot region. The rigid or semi-rigid platform is configured to support portions of the user's foot. The apparatus also comprises a first support structure arranged in the midfoot region of the rigid or semi-rigid platform and laterally extending from the fifth-toe side to a portion of the midfoot region of the rigid or semi-rigid platform. The first support structure has a first height at the fifth-toe side and a second height at the portion of the midfoot region. Additionally, the first height is greater than the second height, and the height of the first support structure tapers in a direction from the fifth-toe side to the midfoot region. Additionally, the first support structure is configured to contact and support at least a fifth toe, fourth toe, and third toe of the user's foot. The apparatus also comprises a lateral abutment arranged in the forefoot region of the rigid or semi-rigid platform and extending vertically from the rigid or semi-rigid platform near the first-toe side. The lateral abutment is configured to laterally support the user's foot at the first toe.

In Example 2, the apparatus of Example 1 further comprises a second support structure arranged in the rearfoot region of the rigid or semi-rigid platform and laterally extending from the portion of the midfoot region to the fifth-toe side to of the rigid or semi-rigid platform. The second support structure includes a third height at the fifth-toe side and a fourth height at the portion of the midfoot region. The fourth height being greater than the third height and tapering therebetween, and the second support structure is configured to contact and support a portion of the user's heel.

In Example 3, the apparatus of Examples 1 or 2, wherein the rigid or semi-rigid platform includes an upper surface configured to contact portions of the user's foot, and portions of the user's foot between the first support structure and the second support structure contact the upper surface of the rigid or semi-rigid platform.

In Example 4, the apparatus of Examples 1-3, wherein the first support structure and the lateral abutment are further configured to offset a position of the user's foot on the forefoot region of the rigid of semi-rigid platform at an angle between 10 and 40 degrees with respect to a position of the user's foot on the rearfoot region of the rigid or semi-rigid platform.

In Example 5, the apparatus of Examples 1-4, wherein the tapering of the first support structure is further configured to elevate and support a fifth metatarsophalangeal joint of the user at fifth height above the rigid or semi-rigid platform, elevate and support a fourth metatarsophalangeal joint of the user at sixth height above the rigid or semi-rigid platform, and elevate and support a third metatarsophalangeal joint of the user at seventh height above the rigid or semi-rigid platform, the fifth height being greater than the sixth height, and the sixth height being greater than the seventh height.

In Example 6, the apparatus of Examples 1-5, wherein the lateral abutment is further configured to apply a force against the user's foot to maintain positioning of the fifth toe, the fourth toe, and the third toe of the user's foot on the first support structure.

In Example 7, the apparatus of Examples 1-6, further comprises a heel abutment arranged at the rearfoot region of the rigid or semi-rigid platform and extending vertically therefrom, and wherein the lateral abutment and the heel abutment are further configured to apply a force against the user's foot to maintain positioning of the fifth toe, the fourth toe, and the third toe of the user's foot on the first support structure.

In Example 8, the apparatus of Examples 1-7, wherein the rigid or semi-rigid platform includes an upper surface configured to contact portions of the user's foot, and one or more portions of the forefoot region, the midfoot region, and the rearfoot region of the rigid or semi-rigid platform are recessed with respect to other portions of the forefoot region, the midfoot region, and the rearfoot region of the rigid or semi-rigid platform.

In Example 9, the apparatus of Examples 8, wherein the first-toe side and the fifth-toe side are configured to laterally stabilize the user's foot.

In Example 10, the apparatus of Examples 1-9, wherein the rigid or semi-rigid platform includes an upper surface configured to contact portions of the user's foot, and the tapering between the first height and the second height of the first support structure increases at an angle between 10 and 40 degrees from the upper surface.

In Example 11, the apparatus of Examples 1-11, further comprises a toe-strap arranged at the forefoot region of the rigid or semi-rigid platform and configured to stabilize the first toe of the user and a position of the user's foot on the forefoot region of the rigid or semi-rigid platform at an angle between 10 and 40 degrees with respect to a position of the user's foot on the rearfoot region of the rigid or semi-rigid platform.

In Example 12, the apparatus of Examples 1-11, further comprises an ankle support structure configured to stabilize an ankle of the user and offset a position of the user's foot on the forefoot region of the rigid or semi-rigid platform at an angle between 10 and 40 degrees with respect to a position the user's foot on the rearfoot region of the rigid or semi-rigid platform.

In Example 13, the apparatus of Examples 1-12, wherein the ankle support structure extends vertically from the rigid or semi-rigid platform.

In Example 14, the apparatus of Examples 1-13, further comprises an ankle support structure arranged at the first-toe side of the rearfoot portion of the rigid or semi-rigid platform and configured to stabilize an ankle of the user. Example 14 also further comprises a foot strap having a first connection arranged on the rearfoot portion and a second connection arranged on the forefoot portion of the rigid or semi-rigid platform, and wherein the ankle support and foot strap are configured to offset a position of the user's foot on the forefoot region of the rigid or semi-rigid platform at an angle between 10 and 40 degrees with respect to a position of the user's foot on the rearfoot region of the rigid or semi-rigid platform.

In Example 15, a method of positioning a user's foot. The method comprises providing a rigid or semi-rigid platform having a first-toe side, a fifth-toe side laterally opposite the first-toe region, a forefoot region, a midfoot region, and a rearfoot region, the rigid or semi-rigid platform is configured to support portions of the user's foot. The rigid or semi-rigid platform includes a first support structure arranged in the midfoot region of the rigid or semi-rigid platform and laterally extending from the fifth-toe side to a portion of the midfoot region of the rigid or semi-rigid platform. The first support structure has a first height at the fifth-toe side and a second height at the portion of the midfoot region. The first height is greater than the second height, and the height of the first support structure tapers in a direction from the fifth-toe side to the midfoot region. The rigid or semi-rigid platform also includes a lateral abutment arranged in the forefoot region of the rigid or semi-rigid platform and extending vertically from the rigid or semi-rigid platform near the first-toe side. The method also comprises aligning the user's foot on first support structure to contact and support at least a fifth toe, fourth toe, and third toe of the user's foot; and aligning the user's foot on the lateral abutment to laterally support the user's foot at the first toe.

In Example 16, the method of Example 15, further comprises a step of stabilizing the first toe of the user and offset a position of the user's foot on the forefoot region of the rigid or semi-rigid platform at an angle between 10 and 40 degrees with respect to a position of the user's foot on the rearfoot region of the rigid or semi-rigid platform via a toe-strap arranged at the forefoot region of the rigid or semi-rigid platform.

In Example 17, the method of Example 15 or 16, further comprises a step of offsetting a position of the user's foot on the forefoot region of the rigid or semi-rigid platform at an angle between 10 and 40 degrees with respect to a position of the user's foot on the rearfoot region of the rigid or semi-rigid platform via a foot strap having a first connection arranged on the rearfoot portion and a second connection arranged on the forefoot portion of the rigid or semi-rigid platform.

In Example 18, the method of Example 15-17, wherein aligning the user's foot on the lateral abutment to laterally support the user's foot at the first toe forces the user's foot to maintain positioning of the fifth toe, the fourth toe, and the third toe of the user's foot on the first support structure.

In Example 19, a method of positioning a user's foot. The method comprises providing a rigid or semi-rigid platform having a first-toe side, a fifth-toe side laterally opposite the first-toe region, a forefoot region, a midfoot region, and a rearfoot region, the rigid or semi-rigid platform is configured to support portions of the user's foot. The rigid or semi-rigid platform includes a first support structure arranged in the midfoot region of the rigid or semi-rigid platform and laterally extending from the fifth-toe side to a portion of the midfoot region of the rigid or semi-rigid platform. The first support structure has a first height at the fifth-toe side and a second height at the portion of the midfoot region. The first height is greater than the second height, and the height of the first support structure tapers in a direction from the fifth-toe side to the midfoot region. The rigid or semi-rigid platform also includes a lateral abutment arranged in the forefoot region of the rigid or semi-rigid platform and extending vertically from the rigid or semi-rigid platform near the first-toe side. The rigid or semi-rigid platform also includes an ankle support structure arranged at the first-toe side of the rearfoot portion of the rigid or semi-rigid platform and configured to stabilize an ankle of the user. The method also comprises aligning the user's foot on first support structure to contact and support at least a fifth toe, fourth toe, and third toe of the user's foot; aligning the user's foot on the lateral abutment to laterally support the user's foot at the first toe, and aligning the user's foot and ankle on the rigid or semi-rigid platform. Further, the method comprises offsetting a position of the user's foot on the forefoot region of the rigid or semi-rigid platform with respect to a position of user's foot on the rearfoot region of the rigid or semi-rigid platform.

In Example 20, the method of Example 19, wherein the steps of restraining and offsetting comprise restraining the user's foot and ankle via a foot strap having a first connection arranged on the rearfoot portion and a second connection arranged on the forefoot portion of the rigid or semi-rigid platform.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various aspects of the present disclosure are directed toward altering a foot position of a person to provide for an optimal heel strike and push-off during gait. Certain example embodiments include aligning the foot, ankle, and/or lower leg in a position with multi-planar pressure points in order to specifically stretch the shortened, stronger muscles of pronation. As a result, various aspects of the present disclosure are directed toward mitigation of foot pronation and/or pain that may occur as a result of muscle imbalance among the foot's dynamic components by proper alignment of the foot, ankle, and/or lower leg.

Figure 1A:
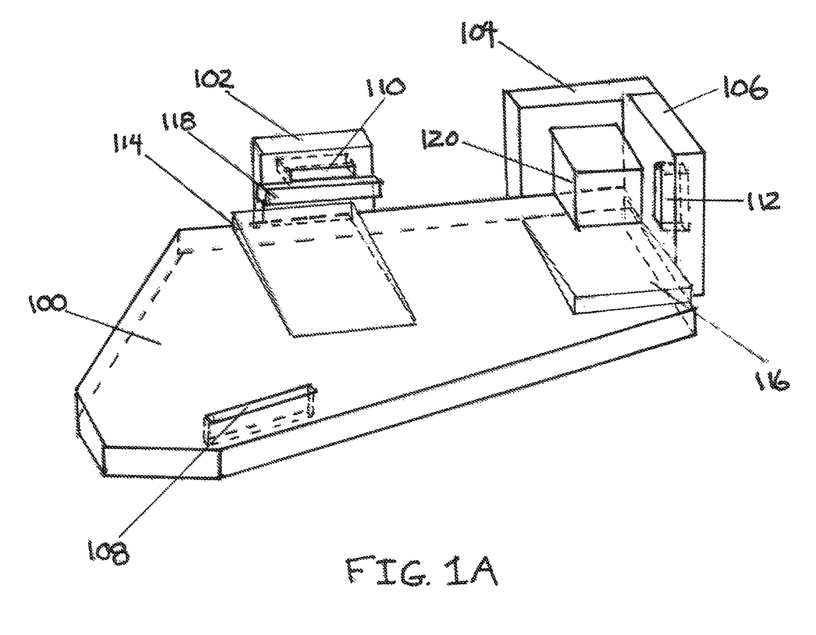
FIG. 1A shows an exemplary apparatus for positioning a user's foot that can be used in relation to embodiments of the present invention.

FIG. 1A shows an exemplary apparatus for positioning a user's foot that can be used in relation to embodiments of the present invention. The apparatus includes a rigid or semi-rigid platform 100 that supports various portions of the user's foot. The rigid or semi-rigid platform 100 shown in FIG. 1A is provided for the user's right foot. The other aspects that form parts of the apparatus shown in FIG. 1A are described relative to a right foot of the user. One skilled in the art will appreciate that a left foot apparatus is constructed and formed in a mirrored configuration to that of the right foot apparatus. As such, the various aspects of the apparatus, and the positioning of the aspects on the apparatus, are described relative to a first-toe side (e.g., largest toe) and a fifth-toe side (e.g., smallest toe). Similarly, the rigid or semi-rigid platform 100 is separated into regions that correspond to portions of the user's foot. These portions include a forefoot region, a midfoot region, and a rearfoot region.

The apparatus shown in FIG. 1A includes a lateral abutment 102 arranged in the forefoot region of the rigid or semi-rigid platform 100. The lateral abutment 102 extends vertically from the rigid or semi-rigid platform 100, and laterally supports the user's foot at the fifth toe side. The lateral abutment 102, in certain embodiments, can include an additional lateral extension 118 to further support the user's foot at the fifth toe side. Additionally, a heel abutment 104 and rearfoot abutment 106 can be included on the rigid or semi-rigid platform 100, in certain embodiments, to laterally support the user's foot at the rear of the foot, and the rear of the first toe side. Similar to the lateral abutment 102, the heel abutment 104 and the rearfoot abutment 106 can include an additional lateral extension 120. As is shown in further detail in FIG. 1B, openings 108/110/112 can be provided as throughputs for a stabilization strap.

The apparatus shown in FIG. 1A also includes a first support structure 114 is provided in the midfoot region of the rigid or semi-rigid platform 100. The first support structure 114 laterally extends from the fifth-toe side to a portion of the midfoot region of the rigid or semi-rigid platform 100, and tapers in a direction from the fifth-toe side to the midfoot region. In certain embodiments, the first support structure 114 contacts and supports at least a fifth toe, fourth toe, and third toe of the user's foot. Additionally, the rigid or semi-rigid platform 100 can include a second support structure 116 in the rearfoot region. The second support structure 116 laterally extends from the first-toe side to a portion of the midfoot region of the rigid or semi-rigid platform 100, and tapers in a direction from the first-toe side to the midfoot region.

Figure 1B:
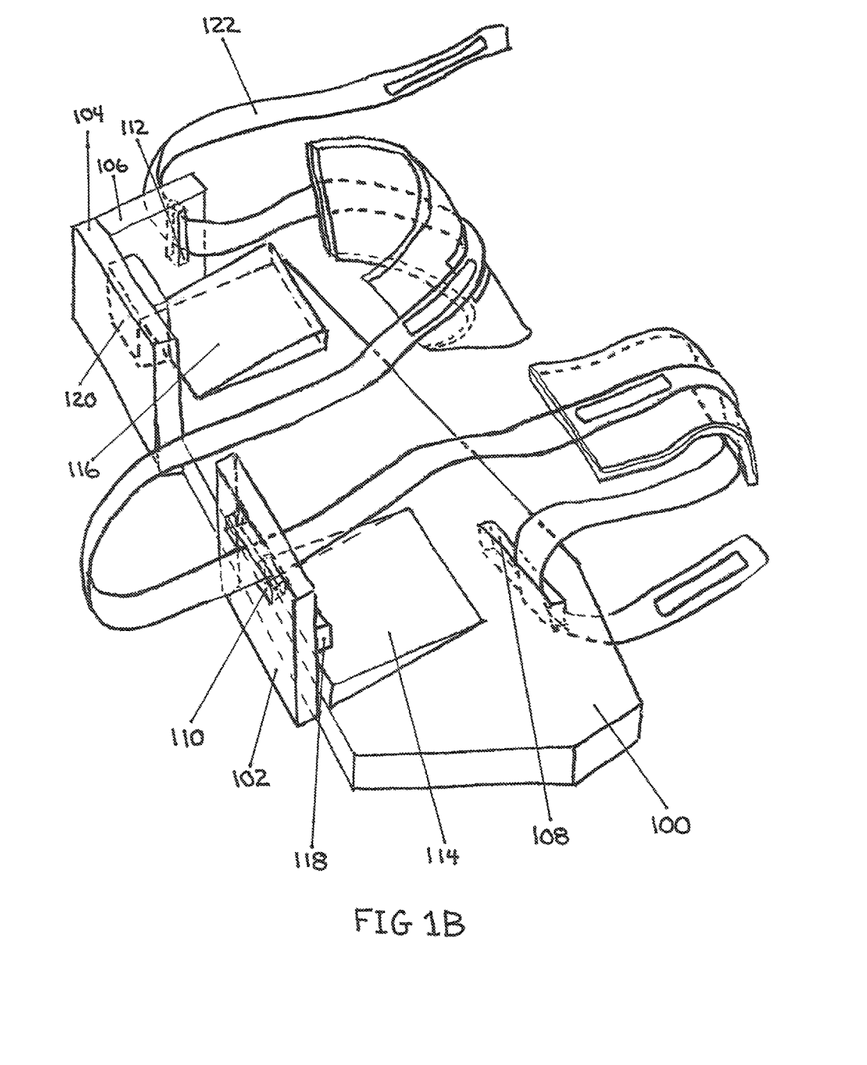
FIG. 1B shows another exemplary apparatus for positioning a user's foot that can be used in relation to embodiments of the present invention.

As is shown in FIG. 1B, a stabilization strap 122 can be provided and connected to various portions of the rigid or semi-rigid platform 100. The stabilization strap 122 secures and further stabilizes a user's foot in a desired position on the first support structure 114, and, in certain embodiments, on the second support structure 116. The stabilization strap 122 is provided through the openings 108/110/112. The positioning of the user's foot can be arranged such that a position of the user's foot on the forefoot region of the rigid or semi-rigid platform 100 is at an angle between 10 and 40 degrees with respect to a position of the user's foot on the rearfoot region of the rigid or semi-rigid platform 100.

Figure 1C:
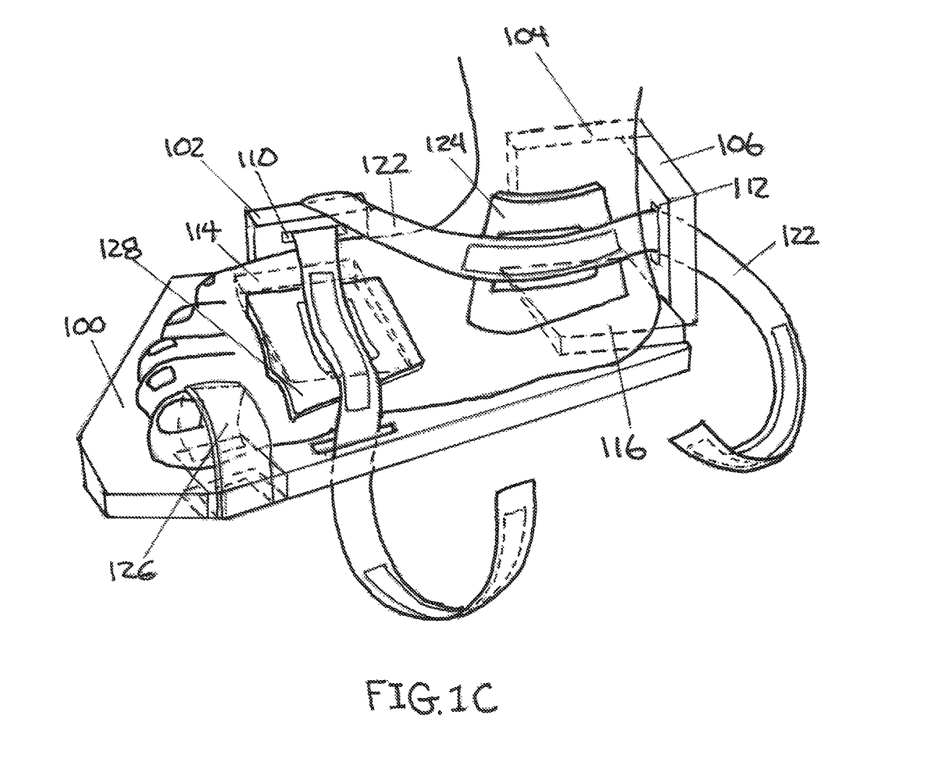
FIG. 1C shows yet another exemplary apparatus for positioning a user's foot that can be used in relation to embodiments of the present invention.

As is shown in FIG. 1C, the user's foot is placed in apparatus, and contacts portions of the rigid or semi-rigid platform 100, the first support structure 114, and the second support structure 116 as secured by the stabilization strap 122. The stabilization strap 122 includes an optional heel cushion 124 to aid in securing of the ankle of the user. Additionally, a toe strap 126 is shown as securing the first toe of the user. The stabilization strap 122 can also be provided with an optional forefoot cushion 128 to apply downward pressure to the top of the foot. The stabilization strap 122 and/or the toe strap 126 can aid in positioning (and securing) the user's foot such that a position of the user's foot on the forefoot region of the rigid or semi-rigid platform 100 is at an angle between 10 and 40 degrees with respect to a position of the user's foot on the rearfoot region of the rigid or semi-rigid platform 100.

Figure 2A:
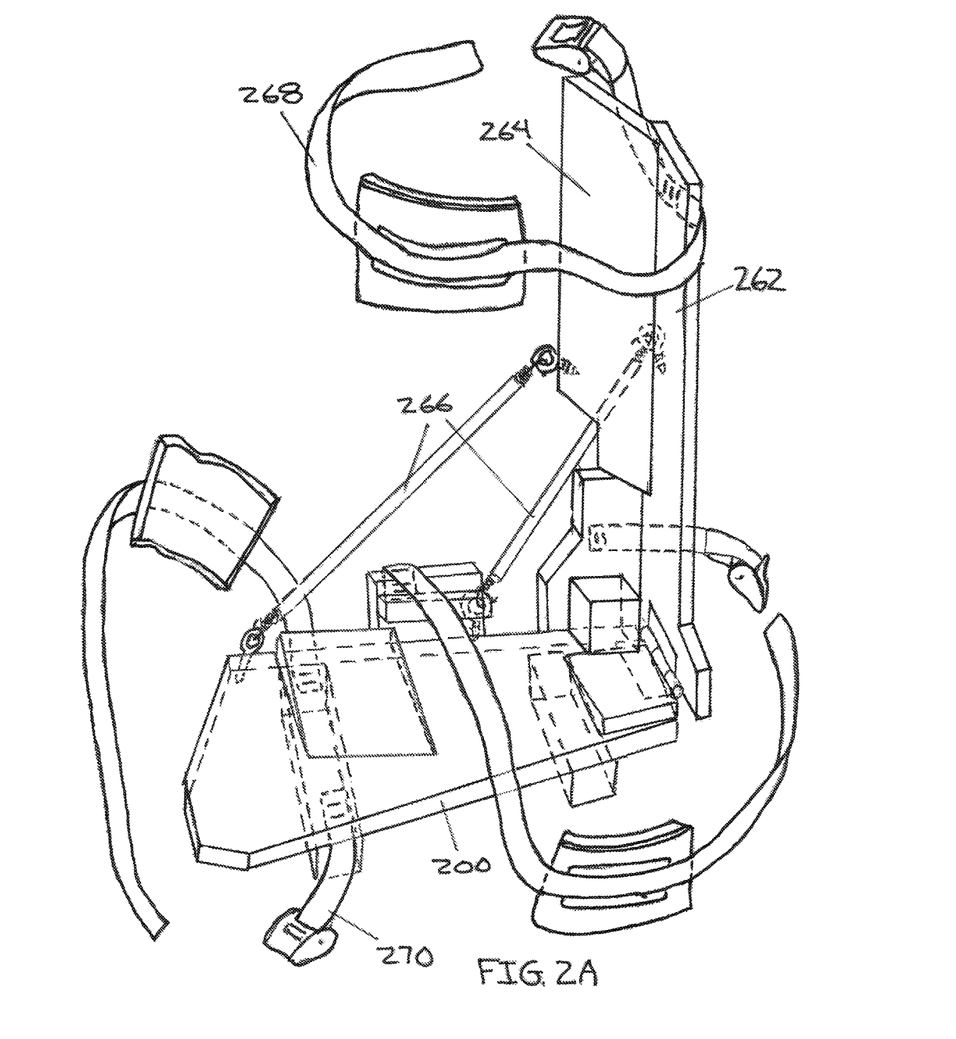
FIG. 2A shows an exemplary apparatus for positioning a user's foot that can be used in relation to embodiments of the present invention.

FIG. 2A shows an exemplary apparatus for positioning a user's foot that can be used in relation to embodiments of the present invention. The apparatus shown in FIG. 2A builds on the aspects shown in FIGS. 1A-C. As in the apparatus shown in FIGS. 1A-C, the apparatus includes a rigid or semi-rigid platform 200. Extending vertically from the rearfoot portion of the rigid or semi-rigid platform 200, and connected to the rigid or semi-rigid platform 200 is an ankle support structure 262 that extends along the rear of the user's calf. The ankle support structure 262 includes a lateral portion 264 that extends around the lateral portion of the user's calf. The rigid or semi-rigid platform 200 is also connected to the ankle support structure 262 by two resistance cords 266. The two resistance cords 266 provide for a selective intensity of an active resistance strengthening of the plantar flexors of the user's foot. The user's foot and ankle are secured and stabilized in the apparatus by a stabilization straps 268 and a toe strap 270. Mobilizing the stabilization strap 268 causes the user's ankle to be immobilized forward and laterally.

Figure 2B:
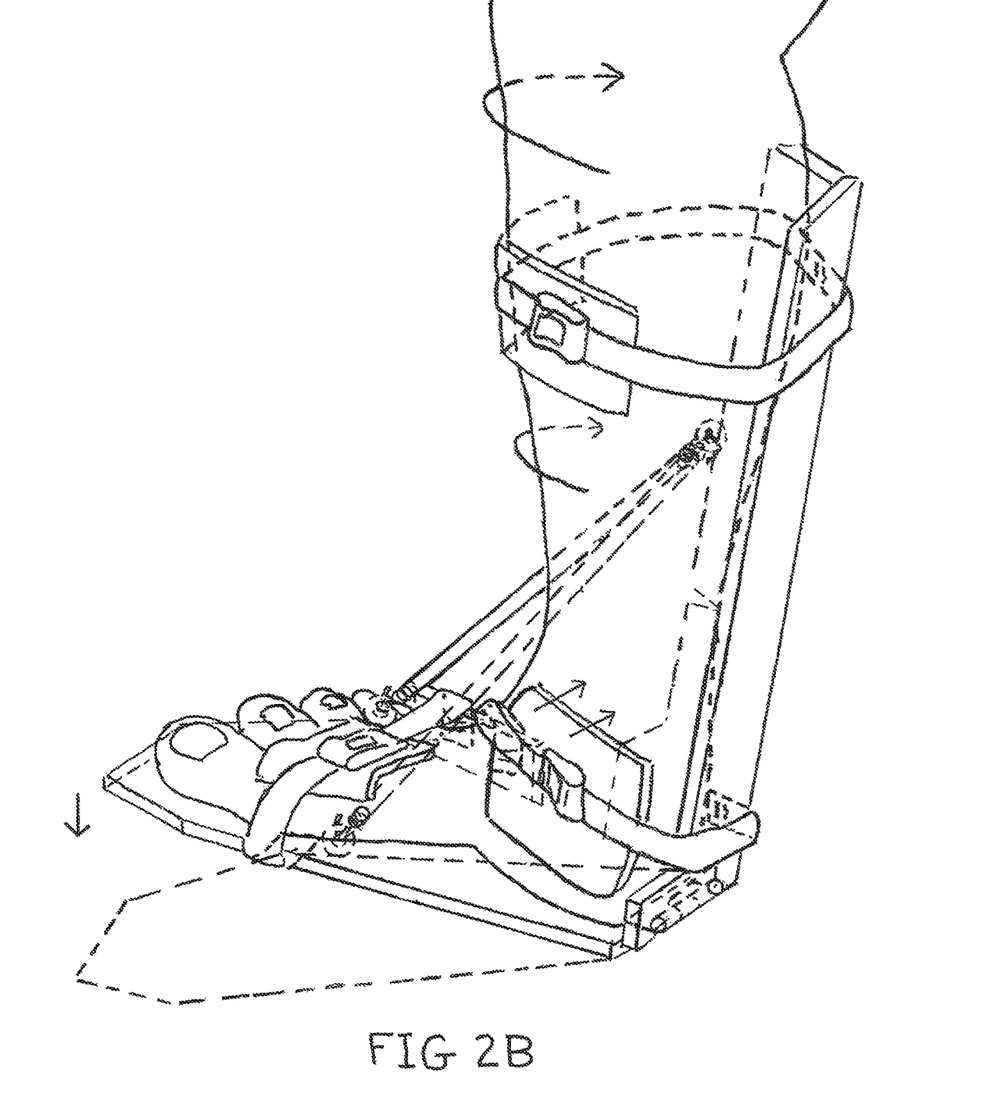
FIG. 2B shows the exemplary apparatus for positioning a user's foot shown in FIG. 2A with a user's foot position therein, that can be used in relation to embodiments of the present invention.

FIG. 2B shows the exemplary apparatus for positioning a user's foot shown in FIG. 2A with a user's foot position therein, that can be used in relation to embodiments of the present invention.

Figure 3A:
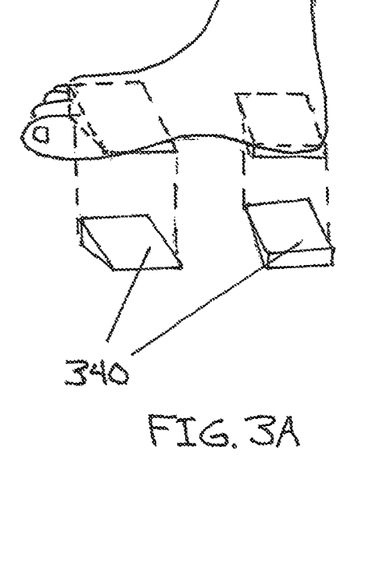
FIG. 3A shows a user's foot positioning as related to embodiments of the present invention.

FIG. 3A shows a user's foot positioning as related to embodiments of the present invention. Two oppositely tapering support structures 340 are shown relative to positions for contacting a user's foot. The forefoot one of the oppositely tapering support structures 340 contacts at least a fifth toe, fourth toe, and third toe of the user's foot, and the rearfoot one of the oppositely tapering support structures 340 contacts between 50% and 100% of the user's heel.

Figure 3B:
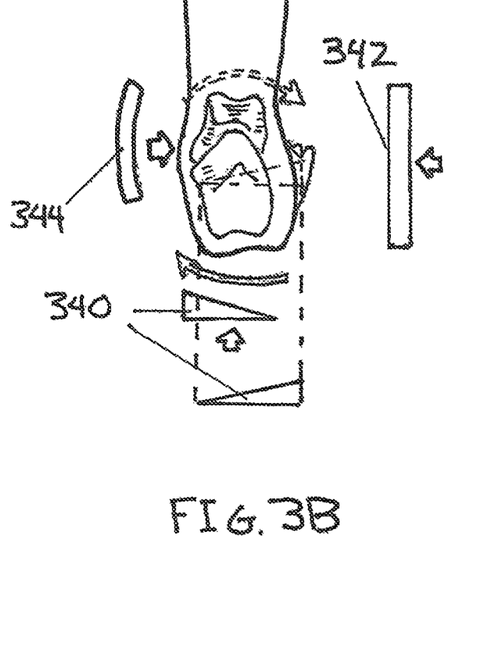
FIG. 3B shows a user's foot positioning as related to embodiments of the present invention.

FIG. 3B shows a user's foot positioning as related to embodiments of the present invention. The oppositely tapering support structures 340 are shown with lateral abutments 342/344. The lateral abutments 342/344 apply counter-pressure to unlock a rigid heel and forefoot.

Figure 4:
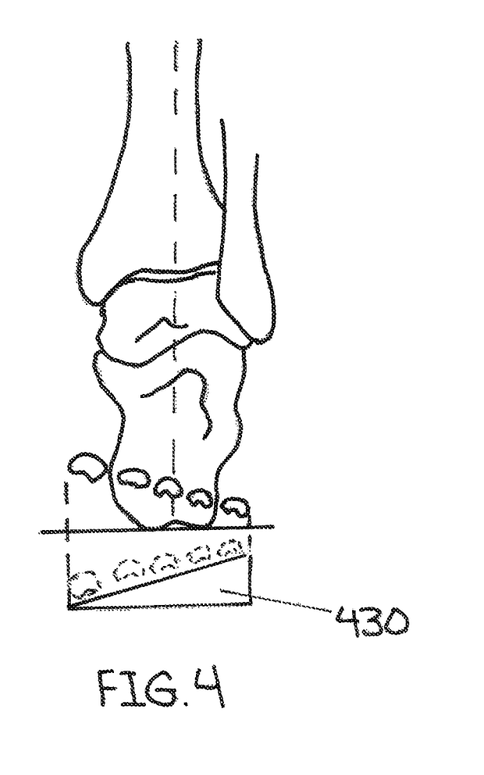
FIG. 4 shows another user's foot positioning as related to embodiments of the present invention.

FIG. 4 shows another user's foot positioning as related to embodiments of the present invention. A user's foot is shown as positioned above a support structure 430. The support structure 430 elevates and supports the forefoot portion of the fifth metatarsophalangeal joint of the user at height above that of the forefoot portion of the fourth metatarsophalangeal joint. Additionally, the support structure 430 elevates and supports the forefoot portion of the fourth metatarsophalangeal joint of the user at height above that of the forefoot portion of the third metatarsophalangeal joint, the forefoot portion of the third metatarsophalangeal joint at a height above the forefoot portion of the second metatarsophalangeal joint, and the forefoot portion of the second metatarsophalangeal joint at a height above the forefoot portion of the first metatarsophalangeal joint.

Figure 5A:
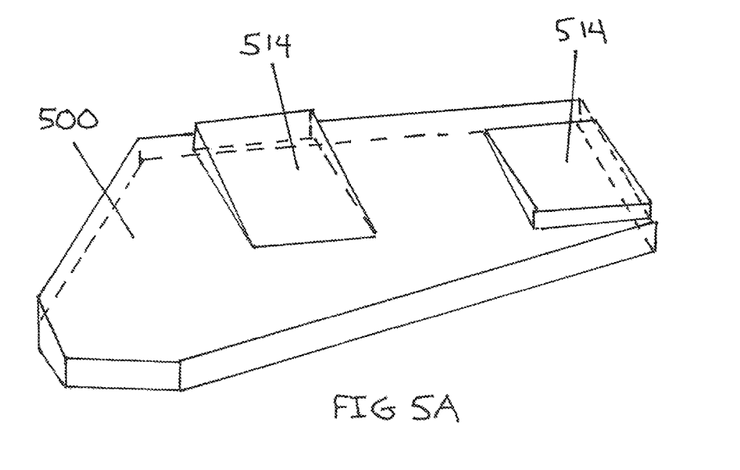
FIG. 5A shows an exemplary apparatus for positioning a user's foot that can be used in relation to embodiments of the present invention.
Figure 5B:
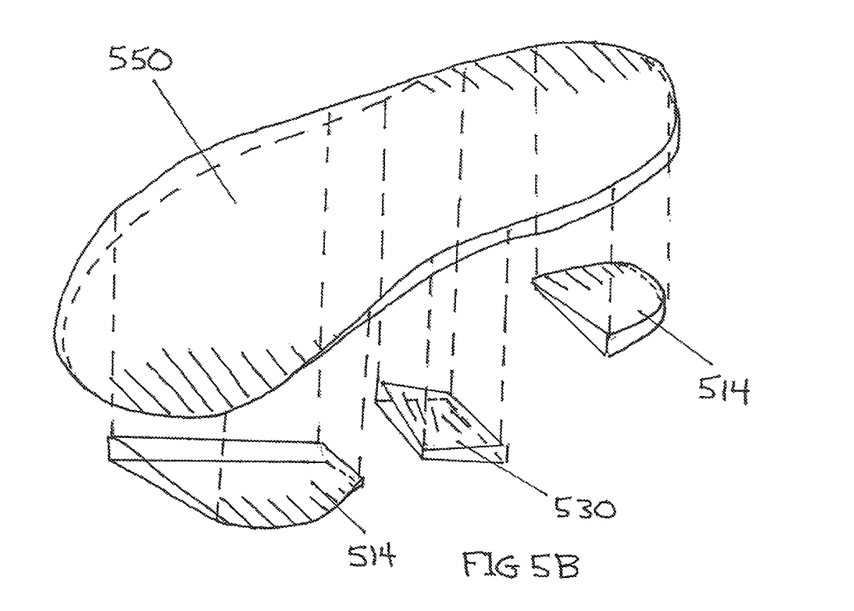
FIG. 5B shows another exemplary apparatus for positioning a user's foot that can be used in relation to embodiments of the present invention.

FIG. 5A shows an exemplary apparatus for positioning a user's foot that can be used in relation to embodiments of the present invention. Two oppositely tapered support structures 514 are shown on a rigid or semi-rigid platform 500. A top surface of the rigid or semi-rigid platform 500 may be recessed, as is shown in FIG. 5B, with respect to its surrounding edges. In this manner, the surface of a user's foot that contacts the oppositely tapered support structures 514 and portions of the rigid or semi-rigid platform 500 can be recessed, and laterally supported by the surround edges of the rigid or semi-rigid platform 500. This structure can be used as an insert for a shoe or boot (as is known in the art). In this manner, the inner surfaces of the shoe or boot can aid in stabilizing a user's foot in a position on the oppositely tapered support structures 514.

FIG. 5B shows a recessed surface 550 for stabilizing a user's foot in a position on the oppositely tapered support structures 514. The recessed surface 550 provides raised edges that cup the user's food and provide a lateral stabilizing force. Additionally, as shown in FIG. 5B, the recessed surface 550 also includes a medial taper 530. The arrangement of the forward one of the oppositely tapered support structures 514 shown in FIG. 5B arranges the fifth metatarsophalangeal joint of the user at height above that of the forefoot portion of the fourth metatarsophalangeal joint. Additionally, The arrangement of the forward one of the oppositely tapered support structures 514 elevates and supports the forefoot portion of the fourth metatarsophalangeal joint of the user at height above that of the forefoot portion of the third metatarsophalangeal joint, the forefoot portion of the third metatarsophalangeal joint at a height above the forefoot portion of the second metatarsophalangeal joint, and the forefoot portion of the second metatarsophalangeal joint at a height above the forefoot portion of the first metatarsophalangeal joint.

Various aspects of the present disclosure include a support structure placed on a rigid or semi-rigid platform that tapers from a lateral position to a medial position. This support structure is limited to a forward region of a rigid or semi-rigid platform, and can taper 40% of the width of the rigid or semi-rigid platform. In certain embodiments, the support structure tapers 50% of the width of the rigid or semi-rigid platform. In other embodiments, the support structure tapers 60% of the width of the rigid or semi-rigid platform. In other embodiments, one or more of the support structures can have differing tapers. Further, one or more of the support structures can taper 70% of the width of the rigid or semi-rigid platform. In other embodiments, one or more of the support structures can taper 80% of the width of the rigid or semi-rigid platform, and in other embodiments, one or more of the support structures can taper 90% or up to 100% of the width of the rigid or semi-rigid platform. Further, in other embodiments of the present disclosure, a second support structure is provided. The second support structure is limited to a rear region of rigid or semi-rigid platform. Additionally, the second support structure oppositely tapers that of the first support structure. In certain embodiments, the second support structure tapers medially to laterally of the rigid or semi-rigid platform. In other embodiments, the support structures are disconnected. In certain embodiments, a gap is provided between the support structures of 1 inch. In other embodiments, a gap is provided between the support structures of 2 inches. In yet other embodiments, a gap is provided between the support structures of 3 inches. Other dimensions are also contemplated.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. An apparatus for positioning a user's foot, the apparatus comprising:
   a rigid or semi-rigid platform having a first-toe side, a fifth-toe side laterally opposite the first-toe side, a forefoot region, a midfoot region, and a rearfoot region, the rigid or semi-rigid platform being configured to support portions of the user's foot;
   a first support structure in the forefoot region of the rigid or semi-rigid platform and laterally extending from the fifth-toe side to a portion of the forefoot region of the rigid or semi-rigid platform, the first support structure providing a surface having a first height at the fifth-toe side and a second height at the portion of the forefoot region, the first height being greater than the second height and the height of the surface provided by the first support structure tapering therebetween in a medial direction from the fifth-toe side, and the surface provided by the first support structure being configured to contact and support at least a fifth toe, fourth toe, and third toe of the user's foot, and wherein the height of the entire surface provided by the first support structure is greater than or equal to a height of any forefoot region portion between the first support structure and the first-toe side, and wherein the tapering of the first support structure is further configured to:
   elevate and support a fifth metatarsophalangeal joint of the user at fifth height above the rigid or semi-rigid platform,
   elevate and support a fourth metatarsophalangeal joint of the user at sixth height above the rigid or semi-rigid platform, elevate and support a third metatarsophalangeal joint of the user at seventh height above the rigid or semi-rigid platform, and elevate and support a second metatarsophalangeal joint of the user at an eight height above the rigid or semi-rigid platform, the fifth height being greater than the sixth height, and the sixth height being greater than the seventh height, and the seventh height is greater than the eighth height; and a second support structure arranged in the rearfoot region of the rigid or semi-rigid platform and laterally extending from the first-toe side to a portion of the rearfoot region of the rigid or semi-rigid platform, the second support structure providing a surface having a third height at the first-toe side and a fourth height at the portion of the rearfoot region, the fourth height being less than the third height and tapering therebetween, wherein the height of the entire surface provided by the second support structure is greater than or equal to a height of any rearfoot region portion between the second support structure and the fifth-toe side, and the surface provided by the second support structure is configured to contact and support a portion of the user's heel.

2. The apparatus of claim 1, wherein the rigid or semi-rigid platform includes an upper surface configured to contact portions of the user's foot, and portions of the user's foot between the first support structure and the second support structure contact the upper surface of the rigid or semi-rigid platform.

3. The apparatus of claim 1, wherein the first support structure is configured to offset a position of the user's foot on the forefoot region of the rigid or semi-rigid platform at an angle between 10 and 40 degrees with respect to a position of the user's foot on the rearfoot region of the rigid or semi-rigid platform.

4. The apparatus of claim 1, and further including a lateral abutment extending vertically from the rigid or semi-rigid platform near the fifth-toe side, the lateral abutment configured to laterally support the user's foot at the fifth toe.

5. The apparatus of claim 4, further comprising a heel abutment arranged at the rearfoot region of the rigid or semi-rigid platform and extending vertically therefrom, and wherein the lateral abutment and the heel abutment are further configured to apply a force against the user's foot to maintain a position of a medial forefoot edge between an angle of 10 and 40 degrees medially with respect to a position of a medial rearfoot edge.

6. The apparatus of claim 1, wherein the rigid or semi-rigid platform includes an upper surface configured to contact portions of the user's foot, and one or more portions of the forefoot region, the midfoot region, and the rearfoot region of the rigid or semi-rigid platform are recessed with respect to other portions of the forefoot region, the midfoot region, and the rearfoot region of the rigid or semi-rigid platform.

7. The apparatus of claim 6, wherein the first-toe side and the fifth-toe side are configured to laterally stabilize the user's foot.

8. The apparatus of claim 1, further comprising a toe-strap arranged at the forefoot region of the rigid or semi-rigid platform and configured to stabilize the first toe of the user and a position of the user's foot on the forefoot region of the rigid or semi-rigid platform at an angle between 10 and 40 degrees with respect to a position of the user's foot on the rearfoot region of the rigid or semi-rigid platform.

9. The apparatus of claim 1, further comprising an ankle support structure configured to stabilize an ankle of the user and offset a position of the user's foot on the forefoot region of the rigid or semi-rigid platform at an angle between 10 and 40 degrees with respect to a position the user's foot on the rearfoot region of the rigid or semi-rigid platform.

10. The apparatus of claim 9, wherein the ankle support structure extends vertically from the rigid or semi-rigid platform.

11. The apparatus of claim 1, further comprising an ankle support structure arranged at the first-toe side of the rearfoot portion of the rigid or semi-rigid platform and configured to stabilize an ankle of the user, and a foot strap having a first connection arranged on the rearfoot portion and a second connection arranged on the forefoot portion of the rigid or semi-rigid platform, and wherein the ankle support and foot strap are configured to offset a position of the user's foot on the forefoot region of the rigid or semi-rigid platform at an angle between 10 and 40 degrees with respect to a position of the user's foot on the rearfoot region of the rigid or semi-rigid platform.

12. The apparatus of claim 1, wherein the tapering of the first support structure is further configured to elevate and support a first metatarsophalangeal joint of the user at a ninth height above the rigid or semi-rigid platform, and wherein the eighth height is greater than the ninth height.

* * * * *